US00PP35283P2

(12) United States Plant Patent
Shipley

(10) Patent No.: US PP35,283 P2
(45) Date of Patent: Jul. 25, 2023

(54) ***HESPERALOE* HYBRID 'LITTLE GIANT'**

(50) Latin Name: ***Hesperaloe funifera* X *parviflora***
Varietal Denomination: Little Giant

(71) Applicant: Nicholas Benoit Shipley, Tucson, AZ (US)

(72) Inventor: Nicholas Benoit Shipley, Tucson, AZ (US)

( * ) Notice: Subject to any disclaimer, the term of this patent is extended or adjusted under 35 U.S.C. 154(b) by 88 days.

(21) Appl. No.: 17/803,554

(22) Filed: Aug. 26, 2022

(51) Int. Cl.
*A01H 6/12* (2018.01)
*A01H 5/02* (2018.01)

(52) U.S. Cl.
USPC ..... Plt./373

(58) Field of Classification Search
USPC ..... Plt./373
See application file for complete search history.

*Primary Examiner* — Annette H Para

(57) ABSTRACT

A new and distinct *Hesperaloe* hybrid named 'Little Giant' is characterized by moderate size, large pink/cream flowers, 6.5-7.5 ft long spicate racemes, heavy nectar production and excellent growth in both the nursery and in the ground.

2 Drawing Sheets

Latin name: *Hesperaloe funifera* X *parviflora*.
Varietal denomination: 'Little Giant'.

BACKGROUND OF THE INVENTION

The present invention relates to a new and distinct *Hesperaloe* hybrid cultivar. The cultivar is the result of intentional hybridization of a proprietary breeding line of *Hesperaloe funifera* (female parent) with a proprietary breeding line of *Hesperaloe parviflora* (male parent). One plant from the growout of the $F_1$ generation was a smaller plant than the female parent with flowers like the male parent as well as a having generally attractive form with fast growth and a long bloom period was selected for asexual propagation and is the object of this application.

SUMMARY OF THE INVENTION

Among the features that distinguish the new *Hesperaloe* hybrid cultivar from all other available and commercial similar looking varieties of *Hesperaloe* known to the inventor are the following combination of characteristics: medium sized plants compared to the range in size of *Hesperaloe* species and cultivars, long bloom period from spring to early summer, large pink/cream flowers, attractive, compact plant form with erect to slightly spreading inflorescences, pink/cream colored flowers, excellent nectar production for pollinators, fast growth and no known disease or insect problems.

*Hesperaloe* hybrid 'Little Giant' has been successfully propagated by division of the multiheaded plant crown at a nursery near Sahuarita, Ariz. and by tissue culture in an independent tissue culture lab.

The foregoing characteristics and distinctions come true to form and are established and transmitted through succeeding propagations. The present invention has not been evaluated under all possible environmental conditions, such that the phenotype may vary with variations in environment without a change in the genotype of the plant.

BRIEF DESCRIPTION OF THE DRAWINGS

The accompanying photographs illustrate *Hesperaloe* hybrid 'Little Giant' growing near Sahuarita, Ariz., depicted in color as nearly correct as it is possible to make in a color illustration of the character.

DETAILED PLANT DESRIPTION

Figure 1:
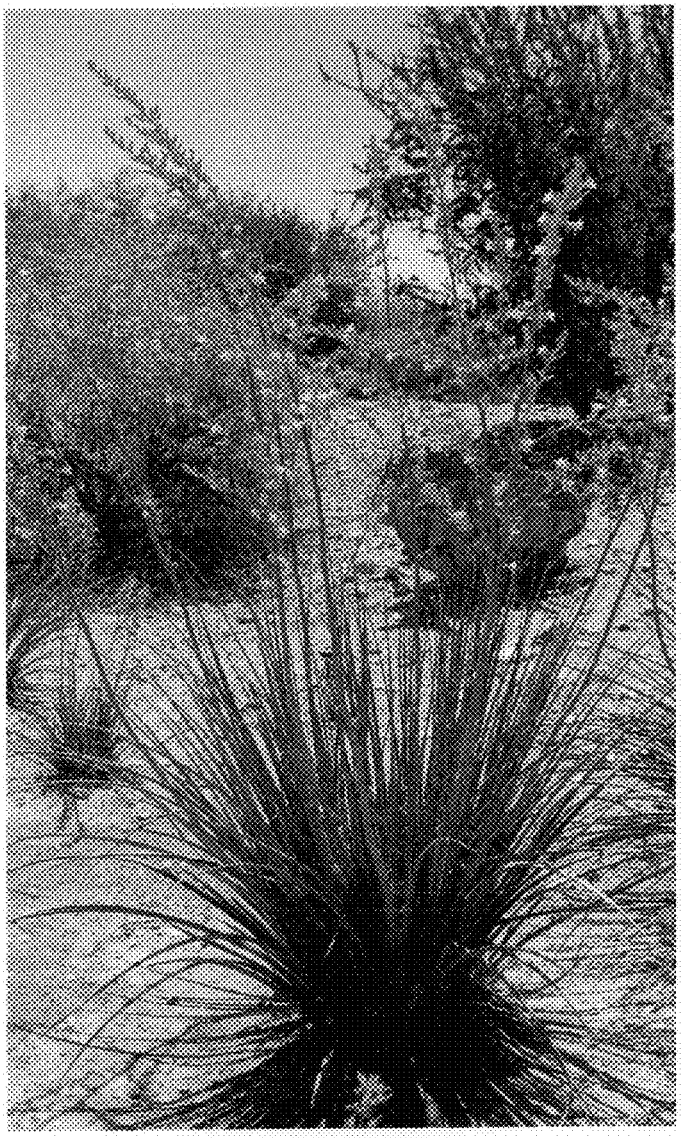
FIG. 1 illustrates *Hesperaloe* hybrid 'Little Giant' aged 5 years growing with irrigation at a commercial nursery near Sahuarita, Ariz.
Figure 2:
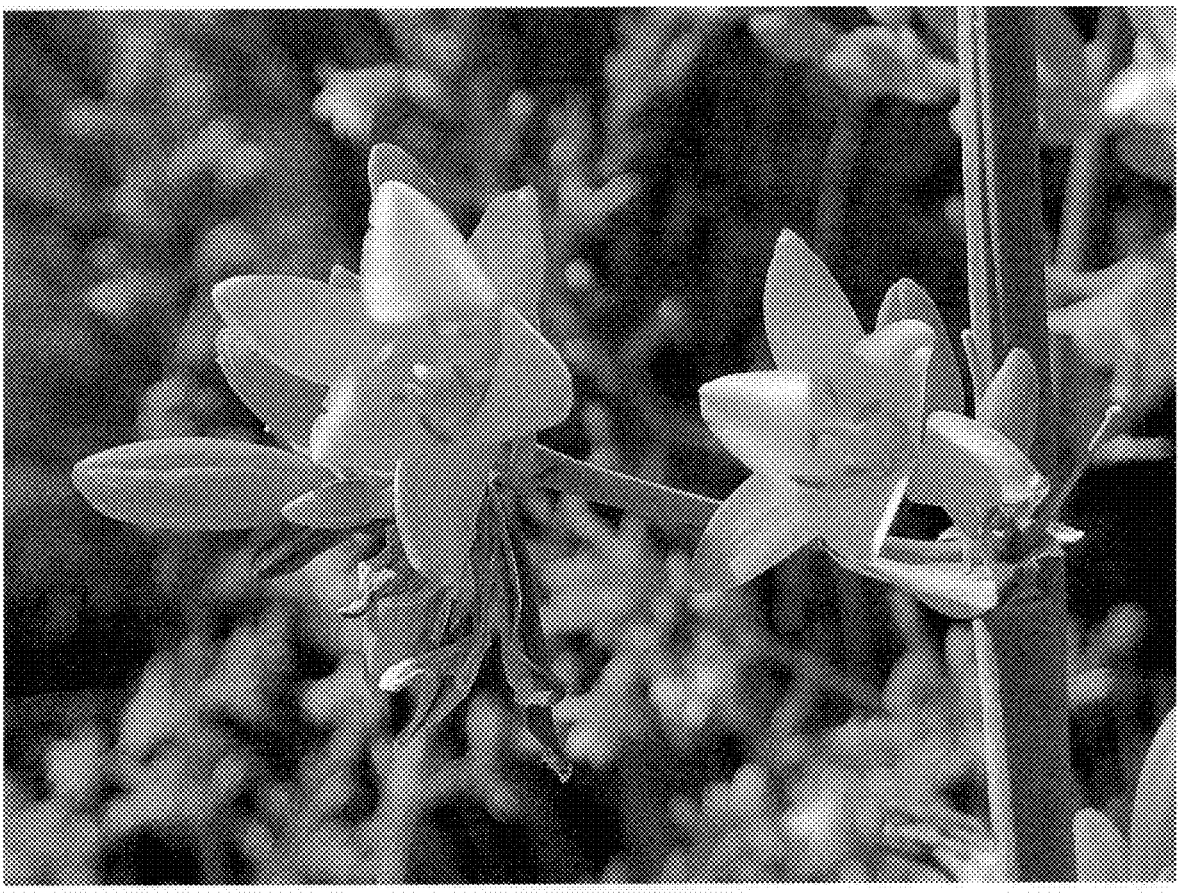
FIG. 2 shows flowers and buds of *Hesperaloe* hybrid 'Little Giant'

The following is a detailed description of the new *Hesperaloe* hybrid plant based upon the original 'Little Giant' plant aged 5 years growing in the ground with irrigation near Sahuarita, Ariz. The color descriptions are based upon the 5$^{th}$ edition RHS Colour Chart, copyright 2007. Color names other than common usage are as listed in *COLOR Universal Language and Dictionary of Names*, by Kenneth L. Kelly and Deane B. Judd; National Bureau of Standards special publication 440. Washington, D.C.: U.S. Department of Commerce, National Bureau of Standards, December 1976.

Plant is a clustering rosette semi-succulent long lived perennial with dark green, narrow, thickened leaves. Flowers are produced on upright, slightly spreading spicate panicles which grow up to about 7 feet long. 'Little Giant' is hardy to −10° F., USDA hardiness zone 6. No disease or insect problems were noted. Numerous species of insects as well as hummingbirds and bats utilize 'Little Giant' flowers as a nectar and pollen source.

At age 5 years foliage of the plant measures about 4 feet tall and 5 feet across not counting the inflorescences. Measured at fully grown inflorescences the plant measures 7 feet tall and 6 feet wide. The examined plant consists of 17 individual rosettes connected to each other below ground level, with from 8-16 leaves each. Ten inflorescences were counted.

Leaves vary in length from 78-135 cm in length, linear and long tapering. The described example was 135 cm long. At the midpoint of this leaf the leaf measured 9 mm wide×10 mm thick (measured top to bottom of the whole leaf). When cut the leaf thickness was 2.8 mm at the midrib tapering to near zero at the margins. The leaves are clasping at the base, fibrous internally, semisucculent and stiff. Leaves other than the basal portion of the leaf are linear, adaxially strongly curled inward from the leaf edges, glabrous excluding the margins, obscurely striate the full length of the leaf (the striations are more easily seen on the adaxial than the abaxial surface), with the surface smooth on both sides of the leaf, the leaf gradually tapers from the base to the acute apex, which is not sharp. The clasping portion of the leaf measures 28 mm wide×8 mm thick, color 155A. The color transitions gradually to 138B on the abaxial surface and 137C on the adaxial surface at 5.5 cm from the leaf base, the color continuing without change up to near the apex, which dries back toward the base with age. Microscopically the leaf color breaks down to alternating bands 0.1-0.2 mm wide of 137A with 0.1 mm wide bands of 138D on the abaxial surface. On the adaxial surface the bands measured 0.2-0.3 mm wide colored 138A alternating. with 0.07-0.1 mm wide bands of 138D. The dried leaf apex is colored 165D. The dried apical portion of the leaf measures 18 cm long and 2 mm thick at its base.

The basal leaf margin has a fragile, hyaline edge about 3 mm wide and nearly transparent, which is lined on the leaf side (axially) with N199D, about 1 mm wide which runs from the leaf base to about 4 cm from the leaf base, where the hyaline edge gradually transitions into spiral fibers which extend forward and outward from the leaf and when pulled straight measure from 2.5-22.0 cm long. These fibers measure 0.25 mm in diameter with color N155A. The brown (N199D) inner lining of the hyaline margin continues into the entirety of the length of the leaf margins with fibers, located just below the fibers on the leaf side. This lining narrows until it reaches the fiber bearing portion of the leaf. The line axial to the fibers is about 0.25 mm wide in the fibered portion of the leaf and is visible from both leaf surfaces continuing the full length of the leaf. The fibers are scattered along the leaf margins at irregular intervals starting from about 4 cm from the leaf base up to about ⅚ of the length of the leaf from the leaf base.

Flowering of 'Little Giant' occurs from April through July at the Sahuarita, Ariz. locality. Individual flowers last 3-4 days. The spent flowers fall away from the inflorescence within a week after anthesis. No floral aroma was noted.

The inflorescence is an apically blooming, spreading spicate panicle 6.5-7.5 feet long. The peduncle is terete, basally measuring 21 mm in diameter, tapering to 2 mm in diameter at the apical spurs. The peduncle surface is smooth, glabrous and glaucous (especially the lower peduncle). Color is 158B at the peduncle base gradually transitioning to 144A at 25 cm above the base of the inflorescence. The peduncle at that point measures 17 mm in diameter. At 49 cm above the base a second transition to color 186B begins, the transition essentially complete at the first inflorescence branch 118 cm above the base. Peduncle diameter at this point measures 11 mm. The upper inflorescence color (186B) extends through the flowering branches. The inflorescence examined had 6 alternate branches as well as the terminal continuation of the main axis which had flowering like the branches. Branch angle of the inflorescence varies from 40-75°. Most flowering occurs on the upper ½ of the inflorescence. The lower branch bracts measure 16 cm long by 3 cm wide (near the bract base) and are triangular, tapering apically (color 144A). The upper branch bracts measure 3 cm long by 2 cm wide and are orbicular in shape. The intermediate bracts grade in size and shape from the lower ones to the upper ones. The flowering branches range from 13-39 cm in length, and 2-3 mm in diameter. The longest branches are located close to the central part of the blooming portion of the inflorescence, The inflorescence branches bear flowering spurs (shortened spikes) measuring 3-5 mm long and 4-5 mm wide excluding the persistent pedicel remnants, 11-19 mm wide including them. Each spur produces 3-12 flowers. The spurs alternate along the main axis of the inflorescence branches. Internodes on the flowering branches vary from 4 mm to 11 cm in length, the shortest at the branch apex and the longest just above the branch attachment to the peduncle axis. These spurs are subtended by awl-like bracts, these measuring 5 mm wide and 5-8 mm long, color 164C.

The mature buds of *Hesperaloe* 'Little Giant' are ellipsoid in shape, measuring 19 mm in length and 6-9 mm in diameter. The bud surface is glabrous and slightly glaucous, colored N57D. Pedicels are terete, measuring 6-9 mm in length×1 mm in diameter, color N57D.

Flowers are actinomorphic, very nectiferous, opening at night and remaining open through the day, with 3 glabrous sepals and 3 glabrous petals (both fused with the receptacle), which are similar in appearance and color, except the sepals are slightly narrower than the petals. The fully opened flowers are flaring, measuring 27-29 mm in diameter and 20 mm in length. The receptacle (color N57D) is hemispherical in shape and is highly nectiferous. The receptacle measures 3 mm long×4 wide. Sepals are long obovate, measuring 19 mm long×4 mm wide, margin entire, apex rounded acute, basally truncate at the receptacle attachment. Adaxially, the sepals are colored 62C near the margins, grading to 62D along the midrib. The abaxial surface of the sepals is colored N57D.

Petals are ovate, 19 mm long×7 mm wide, margin entire, apex rounded acute. The medial portion of the abaxial surface is glaucescent, colored N59D, grading to 69C inside the marginal bands. The marginal portion of the petal (1.5 mm wide at the petal midpoint, narrower at the petal base and apex) is translucent, color N155B. Adaxially the petals are colored medially 69C grading to 70C inside the translucent margins, which are the same on both surfaces.

Six stamens are attached to the receptacle, each one centered along the axis of a sepal or petal. The stamens are 13-14 mm in length, the filaments terete in cross section. The filaments measure 10-11 mm long, tapering from the base to the anthers, basally 1.5 mm in diameter, apically 0.33 mm in diameter. The color of the filament grades from 69C at the base to 70C at the midpoint and gradually back to 69C at the anther base. The filaments are glabrous. Anthers are dorsifixed just below the middle, nearly erect but slightly curved to the attachment side. Anthers are tardily dehiscent. Anthers are ellipsoid, dorsally compressed. Anthers measure 6 mm long×1.5 mm wide×1 mm thick, color 2C. Pollen is spherical, 30μ in diameter, color 2C.

The Pistil measures 15 mm long. The ovary, containing 3 carpels, color 8D, is ovoid in overall shape measuring 5 mm long×3 mm in diameter and weakly three angled at the middle of the carpels. The terete style (color 155C) measures 10 mm long and is tapers from the base, measuring 1.25 mm in diameter at the base and 0.9 mm at the stigma (color 155C). The stigma is hemispherical measuring 0.9 mm in diameter (color 155C). Fruit is a loculicidal and septicidal 3 carpellate dehiscent capsule. The fruit shape is broadly ovoid/ellipsoid, rounded at the base and apiculate at the apex. At dry maturity the pedicel at the fruit base is 3 mm in diameter. The fruit measures 35-39 mm long and 31 mm in diameter. Fruit exterior is faintly ribbed, the ribs angling apically at an angle of 30-45° radiating from the septums. The fruit surface is irregularly mottled with colors from 199D to 200A, the colors intergrading. Each carpel contains 2 rows of half moon shaped black seeds (203B) stacked inside much like coins in a roll with the flat seed edges facing each other in the centerline of the carpel. Each carpel contains approximately 45 seeds giving a total number of seeds/fruit of approximately 135.

Carpel interior surface is shiny, color 165C marked laterally with 199D where the seed margins were in contact with the carpel wall. The septum portion of the interior carpel surface is indistinguishable from the locule portion. The exterior portion of the septum is shiny and strongly cross ribbed corresponding to the seeds internal to it. The septum measures 32 mm long×10 mm wide at the widest part, color 165D, rounded at the base and apiculate at the apex. Fruit production is rare in 'Little Giant'.

Seeds (203B) are half moon shaped, 9-10 mm long×6-7 mm wide×1.5-2 mm thick at the thickest part. Seed surface is irregularly wrinkled, the wrinkles vaguely radiating away from the hilum and the flat side of the seed. The hilum is irregular in shape, located at the point where the rounded and flat edges of the seed meet and contact the central axis of the fruit. The hilum measures 1-1.5 mm in diameter and is colored 165C.

COMPARISONS TO RELATED HESPERALOES

Compared to its parents, *Hesperaloe* hybrid 'Little Giant' is about half the size of the *Hesperaloe funifera* female parent and has pink flowers instead of the white flowers of the female parent. The leaves of 'Little Giant' are narrower than its female parent. Additionally, *Hesperaloe funifera* is a night bloomer, with flowers closing in the morning while 'Little Giant' flowers open at night but remain open into the daytime, though they do not remain as broadly opened in daytime as they are at night. Compared to the *Hesperaloe parviflora* male parent, 'Little Giant' is about twice as big and has wider leaves. Flowers of both are similarly pink, but 'Little Giant' flowers open wider than those of the male parent.

Compared to *Hesperaloe parviflora* 'Yellow' (unpatented), 'Little Giant' may be distinguished by the different flower color. 'Yellow' has yellow flowers while 'Little Giant' flowers are pink/cream. Additionally, the 'Little Giant' plant is larger than 'Yellow'.

Compared to *Hesperaloe parviflora* 'Desert Flamenco' (not patented), 'Little Giant' has pink/cream flowers while those of 'Desert Flamenco' are bicolored pink/light orange. The plant of 'Desert Flamenco' is smaller than that of 'Little Giant'.

*Hesperaloe campanulata* 'MSWNNuevo Leon' (U.S. Plant Pat. No. 32,069) is compared since *Hesperaloe campanulata* and *parviflora* are similar and related species. 'MSWNNuevo Leon' is a similarly sized plant but the inflorescences grow to 10 feet in height as opposed to the 'Little Giant' 6.5-7.5 foot tall inflorescence. The flowers of 'Little Giant' are triple the size of those of 'MSWNNuevo Leon'. 'MSWNNuevo Leon' has a longer bloom season than 'Little Giant'.

*Hesperaloe parviflora* 'MSWNPerma' (U.S. Plant Pat. No. 28,909) may be distinguished from 'Little Giant' by flower colors. 'MSWNPerma' flowers are bicolored pink/yellow compared to pink/cream on 'Little Giant'. 'MSWNPerma' is a smaller plant than 'Little Giant'. The inflorescence of 'Little Giant' is roughly twice as long as that of 'MSWNPerma'.

*Hesperaloe parviflora* 'Perpa' (U.S. Plant Pat. No. 21,729) has smaller flowers with a different color than 'Little Giant'. 'Little Giant' flowers are colored 62C-62D, N57D, N59D, 69C-69D, N155B while those of 'Perpa' are listed as 53D at full flower opening. 'Perpa' plants are about ½ the size of 'Little Giant' plants. 'Perpa' produces fruits and seeds, while 'Little Giant' is mostly seedless.

*Hesperaloe funifera* X *parviflora* 'Perfu' (U.S. Plant Pat. No. 21,728) has inflorescences 8 feet tall with pink flowers (67C to 67D) arising from a 4 foot wide plant, while 'Little Giant' inflorescences are 6.5-7.5 feet long with pink/cream (62C-62D, N57D, N59D, 69C-69D, N155B) flowers and plants 5 feet wide. The flowers of 'Little Giant' are considerably broader than those of 'Perfu' (27-29 mm compared to 20 mm). The leaves of 'Perfu' are much wider than those of 'Little Giant'.

*Hesperaloe parviflora* 'Coral Glow' (U.S. Plant Pat. No. 29,626) has bicolored peach/yellow flowers compared to the pink/cream flowers of 'Little Giant'. 'Coral Glow' is a smaller plant with inflorescences 6 feet tall compared to 6.5-7.5 feet tall for 'Little Giant'.

*Hesperaloe parviflora* 'MSWNPered' (U.S. Plant Pat. No. 28,910) may be distinguished from 'Little Giant' by its smaller plant size and different flower color 62C-62D, N57D, N59D, 69C-69D, N155B for 'Little Giant' and 53C-D for 'MSWNPered').

*Hesperaloe parviflora* X *funifera* 'Night Lights' (not patented) is a slightly larger plant than 'Little Giant' and has cream colored flowers compared to pink/cream on 'Little Giant'.

*Hesperaloe parviflora* 'Stop Lights' (U.S. Plant Pat. No. 34,195) is a much smaller plant than 'Little Giant' with inflorescences about half as long as those of 'Little Giant'. Flowers of 'Stop Lights' are red compared to the pink/cream flowers of 'Little Giant'.

I claim:

1. A new and distinct variety of *Hesperaloe* hybrid plant named 'Little Giant' substantially as described and illustrated herein.

* * * * *